(12) United States Patent
Warner et al.

(10) Patent No.: US 6,862,125 B2
(45) Date of Patent: Mar. 1, 2005

(54) REVERSIBLE ELECTRO-OPTIC DEVICE EMPLOYING APROTIC MOLTEN SALTS AND METHOD

(75) Inventors: Benjamin P. Warner, Los Alamos, NM (US); T. Mark McCleskey, Los Alamos, NM (US); Anthony K. Burrell, Los Alamos, NM (US); Simon B. Hall, Palmerston North (NZ)

(73) Assignee: The Regents of the University of California, Los Alamos, NM (US)

( * ) Notice: Subject to any disclaimer, the term of this patent is extended or adjusted under 35 U.S.C. 154(b) by 99 days.

(21) Appl. No.: 10/430,780

(22) Filed: May 5, 2003

(65) Prior Publication Data

US 2004/0223207 A1 Nov. 11, 2004

(51) Int. Cl.$^7$ ............... G02F 1/15; G02F 1/00; G02F 1/29; G02F 1/153
(52) U.S. Cl. ............ 359/265; 359/321; 359/318; 359/270; 359/272
(58) Field of Search ............... 359/240–241, 359/247, 250, 253–254, 263, 265, 267, 269, 270–284, 296, 315, 318, 321, 577–578, 601–604, 609, 839, 843; 252/583, 800; 204/290.07; 428/426

(56) References Cited

U.S. PATENT DOCUMENTS

| | | | |
|---|---|---|---|
| 5,056,899 A | 10/1991 | Warszawski | 350/357 |
| 5,128,799 A | 7/1992 | Byker | 359/265 |
| 5,404,244 A | 4/1995 | Van Dine et al. | 359/270 |
| 5,663,829 A | 9/1997 | Lefrou et al. | 359/275 |
| 5,808,778 A | 9/1998 | Bauer et al. | 359/267 |
| 5,827,602 A | 10/1998 | Koch et al. | 429/194 |
| 5,905,590 A | 5/1999 | Van Der Sluis et al. | 359/275 |
| 5,923,456 A * | 7/1999 | Tench et al. | 359/266 |
| 6,111,685 A | 8/2000 | Tench et al. | 359/267 |
| 6,166,847 A | 12/2000 | Tench et al. | 359/266 |
| 6,400,491 B1 * | 6/2002 | Tench et al. | 359/270 |
| 6,420,036 B1 | 7/2002 | Varaprasad et al. | 428/432 |
| 6,535,323 B2 | 3/2003 | Johnson et al. | 359/275 |
| 6,552,843 B1 * | 4/2003 | Tench et al. | 359/321 |
| 2002/0044717 A1 | 4/2002 | Richardson | 385/16 |
| 2003/0063365 A1 | 4/2003 | Wang | 359/265 |

OTHER PUBLICATIONS

Kirk–Othmer, "Antibiotics to Batteries," Encyclopedia of Chemical Technology, Fourth Edition, vol. 3, pp. 1016–1109.

Kirk–Othmer, "Lasers to Mass Spectrometry," Encyclopedia of Chemical Technology, Fourth Edition, vol. 15, pp. 446–447.

J. Sun, M. Forsyth, and D. R. MacFarlane, "Room–Temperature Molten Salts Based on the Quaternary Ammonium Ion," J. Phys. Chem. B, 102, pp. 8858–8864, 1998.

Ira N. Levine, "Physical Chemistry," Second Edition, pp. 389–392, 395, 465, 471, 1983.

Ultraviolet Stabilizers List, Modern Plastics World Encyclopedia, pp. C–120–C–122, 2001.

T. J. Richardson, J. L. Slack, R. D. Armitage, R. Kostecki, B. Farangis, and M. D. Rubin, "Switchable Mirrors Based on Nickel–Magnesium Films," Applied Physics Letters, vol. 78, No. 20, pp. 3047–3049, May 2001.

* cited by examiner

Primary Examiner—Hung Xuan Dang
Assistant Examiner—Joseph Martinez
(74) Attorney, Agent, or Firm—Samuel L. Borkowsky

(57) ABSTRACT

A single-compartment reversible mirror device having a solution of aprotic molten salt, at least one soluble metal-containing species comprising metal capable of being electrodeposited, and at least one anodic compound capable of being oxidized was prepared. The aprotic molten salt is liquid at room temperature and includes lithium and/or quaternary ammonium cations, and anions selected from trifluoromethylsulfonate ($CF_3SO_3^-$), bis(trifluoromethylsulfonyl)imide (($CF_3SO_2)_2N^-$), bis(perfluoroethylsulfonyl)imide (($CF_3CF_2SO_2)_2N^-$) and tris(trifluoromethylsulfonyl)methide (($CF_3SO_2)_3C^-$). A method for preparing substantially pure molten salts is also described.

19 Claims, 1 Drawing Sheet

REVERSIBLE ELECTRO-OPTIC DEVICE EMPLOYING APROTIC MOLTEN SALTS AND METHOD

STATEMENT REGARDING FEDERAL RIGHTS

This invention was made with government support under Contract No. W-7405-ENG-36 awarded by the U.S. Department of Energy. The government has certain rights in the invention.

FIELD OF THE INVENTION

The present invention relates generally to reversible mirrors and more particularly to a reversible mirror employing aprotic molten salts and to molten salt electrolyte solutions.

BACKGROUND OF THE INVENTION

Sunlight transmitted through windows in buildings and transportation vehicles can generate heat (via the greenhouse effect) that creates an uncomfortable environment and increases air conditioning requirements and costs. Current approaches to providing "smart windows" with adjustable transmission for use in various sunlight conditions involve the use of light absorbing materials. These approaches are only partially effective because the window itself is heated and because these devices, such as electrochromic devices, are relatively expensive and exhibit limited durability and cycle life. Another limitation of electrochromic devices is that many employ organic dyes that have limited stability to ultraviolet light; absorb light rather than reflect it and therefore only partially reduce solar thermal burdens; and do not offer privacy or complete opacity. Certain liquid crystal-based window systems switch between transmissive and opaque/scattering states, but these systems require substantial voltages to maintain the transparent state. There is an important need for an inexpensive, durable low voltage smart window with variable reflectivity. Reflecting the light, rather than absorbing it, is the most efficient means for avoiding inside heating. Devices for effectively controlling transmission of light are also needed for a variety of other applications, e.g., energy efficient dimmers for displays.

Bright light from headlamps on following vehicles reflected in automobile rear and side view mirrors is annoying to drivers and creates a safety hazard by impairing driver vision. Currently available automatically dimming mirrors rely on electrochromic reactions to produce electrolyte species that absorb light that would otherwise be reflected from a static mirror. Such devices do not provide close control over the amount of reflected light, and are expensive to fabricate since a very constant inter-electrode spacing is required to provide uniform dimming. Image sharpness is also reduced for electrochromic mirror devices since the reflected light must pass through the electrolyte twice. There is an important need for an inexpensive adjustable mirror device that provides close control of reflected light with minimal image distortion.

In prior art attempts to exploit reversible electrodeposition of a metal for light modulation, the deposits obtained on transparent substrates presented a rough and black, gray, or sometimes colored appearance (typical of finely-divided metals) and exhibited poor reflectivity and high light absorbance, especially when thick. Such deposits have been investigated for display applications involving reflectance from the background, with white pigments often being added to improve contrast. Warszawski (U.S. Pat. No. 5,056,899), which is concerned with displays, teaches that reversible metal electrodeposition is most appropriate for display applications, since significant disadvantages for transmission devices were given (e.g., the possibility of metal electrodeposition at the counter electrode). Such teachings imply that the application of reversible metal electrodeposition to smart windows must involve light absorption by the finely divided electrodeposited metal, which would result in heating of the device itself and thus the space inside.

In addition to the desired electrodeposition of metals, competing and deleterious side-reactions may also occur. If aqueous electrolytes are used with the device, then the oxidation and reduction of water to produce oxygen gas and hydrogen gas, respectively, may occur. These reactions decrease the current efficiency for metal electrodeposition. Importantly, reversible mirror devices are volume-constrained and may rupture if even small amounts of gas are generated. Other unwanted and deleterious side-reactions include formation of metal complexes with hydroxide and oxide ligands, and rapid oxidation of electrodeposited metal.

Some of the problems associated with the use of aqueous electrolytes may be overcome if organic solvents are used instead of water. Reversible mirror devices that employ conventional organic solvents have been described in, for example, U.S. Pat. No. 5,923,456 to D. M. Tench et al. entitled "Reversible Electrochemical Mirror," which issued on Jul. 13, 1999; U.S. Pat. No. 6,111,685 to D. M. Tench et al. entitled "Reversible Electrochemical Mirror (REM) With Improved Electrolyte Solution," which issued Aug. 29, 2000; U.S. Pat. No. 6,166,847 to D. M. Tench et al. entitled "Reversible Electrochemical Mirror for Modulation of Reflected Radiation," which issued Dec. 26, 2000; and U.S. Pat. No. 6,400,491 to D. M. Tench et al. entitled "Fast-Switching Reversible Electrochemical Mirror (REM)," which issued Jun. 4, 2002, all incorporated by reference herein. Organic solvents, however, present their own set of problems for reversible mirrors. These problems may include low solubility of charge carriers in organic solvents, poor conductivity, poor solubility of metal ions, low boiling points, toxicity, flammability, low electrochemical stability, low photostability, and poor seal tolerance. Some organic solvents are reduced (and generate hydrogen gas) more easily than the metal ions are electrodeposited. Additionally, organic solvents that are polar enough to support electro-chemistry may include functional groups such as ketone groups and ester groups that may chemically react with metals and interfere with electrodeposition.

Another reversible mirror employs a permanent thin metal film that becomes transparent upon exposure to hydrogen gas (see, for example, U.S. Pat. No. 6,535,323 to M. T. Johnson et al. entitled "Light-switching device," which issued Mar. 18, 2003; U.S. Pat. No. 5,905,590 to P. Van Der Sluis et al. entitled "Optical switching device comprising switchable hydrides," which issued May 18, 1999; U.S. Patent Application 20020044717 to T. J. Richardson entitled "Electrochromic materials, devices and process of making," which was published Apr. 18, 2002; and T. J. Richardson et al., "Switchable mirrors based on nickel-magnesium films," *Applied Physics Letters,* 2001, 78, 3047–3049, all incorporated by reference herein). These devices operate either by addition and removal of hydrogen gas, which requires gas handling capabilities and the manipulation of highly flammable hydrogen gas, or by electrochemical production of hydrogen gas from highly caustic aqueous solutions.

A reversible mirror that overcomes the disadvantages of known reversible mirrors remains highly desirable.

Therefore, it is an object of the present invention is to provide a reversible mirror that overcomes the disadvantages of known reversible mirrors.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

In accordance with the objects and purposes of the present invention, as embodied and broadly described herein, the present invention includes a single-compartment reversible electro-optic device having as the medium of variable transmittance to light, a solution of aprotic molten salt, at least one soluble metal-containing species having metal capable of being electrodeposited, and at least one anodic compound capable of being oxidized.

The invention also includes a method for preparing a substantially pure aprotic molten salt from an anion precursor and a cation precursor. The method includes preparing an aqueous mixture of cation precursor and decolorizing agent such as charcoal or activated carbon, filtering the mixture, combining the filtrate with anion precursor to form an impure molten salt, removing water from the impure molten salt, and passing the impure molten salt through alumina or silica to form substantially pure molten salt. Molten salts that can be made using this procedure are preferably aprotic molten salts that are liquid at room temperature and include at least one cation selected from group consisting of lithium cation and quaternary ammonium cations, and at least one anion selected from the group consisting of trifluoromethylsulfonate ($CF_3SO_3^-$), bis(trifluoromethylsulfonyl)imide (($CF_3SO_2)_2N^-$), bis(perfluoroethylsulfonyl)imide (($CF_3CF_2SO_2)_2N^-$) and tris(trifluoromethylsulfonyl)methide (($CF_3SO_2)_3C^-$).

The invention also includes a compound having an anion selected from the group consisting of trifluoromethylsulfonate ($CF_3SO_3^-$), bis(trifluoromethylsulfonyl)imide (($CF_3SO_2)_2N^-$), bis(perfluoroethylsulfonyl)imide (($CF_3CF_2SO_2)_2N^-$), and tris(trifluoromethylsulfonyl)methide (($CF_3SO_2)_3C^-$) and a radical cation selected from the group consisting of radical cations of compounds comprising the structural formula

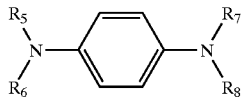

wherein $R_5$, $R_6$, $R_7$ and $R_8$ are the same or different and are each selected from hydrogen, alkyl of 1 to 10 carbon atoms, phenyl optionally substituted at any one position with chloride, bromide, iodide, cyano, or an alkyl group of 1 to 4 carbon atoms, and benzyl, wherein the phenyl moiety of the benzyl group is optionally substituted at any one position with chloride, bromide, iodide, cyano, or an alkyl group of 1 to 4 carbon atoms; radical cations of compounds comprising the structural formula

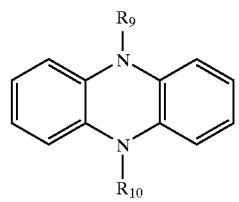

wherein $R_9$ is the same as or different from $R_{10}$ and both $R_9$ and $R_{10}$ are selected from alkyl of 1 to 10 carbon atoms, phenyl optionally substituted at any one position with chloride, bromide, iodide, cyano, or alkyl of 1 to 4 carbon atoms, or benzyl, optionally substituted at any one position of the phenyl group of the benzyl group with chloride, bromide, iodide, cyano, or alkyl of 1 to 4 carbon atoms; radical cations of compounds comprising the structural formula

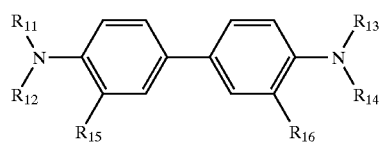

wherein $R_{11}$, $R_{12}$, $R_{13}$ and $R_{14}$ are the same or different and are each selected from alkyl of 1 to 10 carbon atoms or phenyl; and $R_{15}$ and $R_{16}$ are the same or different and are each selected from hydrogen or alkyl of 1 to 10 carbon atoms, provided that both $R_{15}$ and $R_{16}$ are hydrogen or both are alkyl, and if $R_{15}$ and $R_{16}$ are both hydrogen, not more than one of $R_{11}$ and $R_{12}$ is hydrogen and not more than one of $R_{13}$ and $R_{14}$ is hydrogen; radical cations of compounds comprising the structural formula

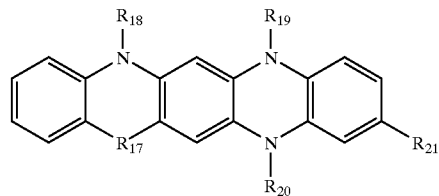

wherein $R_{17}$ is oxygen or sulfur, $R_{21}$ is hydrogen or dialkylamino, wherein the alkyl groups are the same or different and are each selected from alkyl of 1 to 6 carbon atoms, and R18, $R_{19}$ and $R_{20}$ are the same or different and are each selected from hydrogen, alkyl of 1 to 6 carbon atoms, phenyl, optionally substituted at any one position with an alkyl group of 1 to 6 carbon atoms, and benzyl, optionally substituted at any one position of the phenyl group of the benzyl group with an alkyl group of 1 to 6 carbon atoms; radical cations of compounds comprising the structural formula

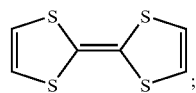

radical cations of compounds comprising the structural formula

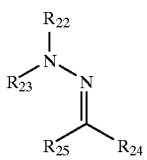

wherein $R_{22}$, $R_{23}$, $R_{24}$ and $R_{25}$ are individually selected from a group consisting of hydrogen, alkyl containing 5 to 20 carbon atoms, alkenyl containing 2 to 20 carbon atoms, alkynyl containing 2 to 20 carbon atoms, and aryl containing 5 to 20 carbon atoms which are unsubstituted or optionally substituted with one or more ester, ether, aryl, amine, thioester, alkyl, alkoxy, alkene, alkyne, cyano, fluoride, chloride, bromide, iodide, organometallocene functional groups, or combinations thereof; radical cations of hydrazone compounds selected from the group consisting of acetone 2,2-dimethylhydrazone, 2-pentanone 2ethyl-2-methylhydrazone, 2-ethylbutanal 1-ethyl-1-propylhydrazone, 2-ethyl-2-nonanone 2-hexyl-2-propylhydrazone, (E)-3-nonen-2-one 2-butyl-2-propylhydrazone, 2-hexanone 2-[(E)-2-butenyl]-2-[(Z)-2-butenyl]-hydrazone, 4-pentyn-2-one 2,2-dipropylhydrazone, 1-penten-3-one 3,3-dimethylhydrazone, 2-hexanone 2,2-diphenylhydrazone, 3-heptanone 3-methyl-3-phenylhydrazone, 1-ethoxy-2-butanone 2-methyl-2-phenylhydrazone, 1-phenylacetone 2-(3-methoxyphenyl)-2-phenylhydrazone, 2-phenacetaldehyde 1-methyl-1-phenylhydrazone, methyl 3-[(Z)-2-methyl-2-phenylhydrazone]-butanethioate, 1-(3-chlorophenyl)-3-methoxy-1-propanone 1-methyl-1-(3-methylphenyl) hydrazone, ferrocenephenylketone 2-[(E)-2-butenyl]-2-[(Z)-2-butenyl]hydrazone, bis(cyclopentadienyl) cobaltmethylketone 2,2-diphenylhydrazone, bis (cyclopentadienyl)dimethylzirconiummethylketone 2,2-diphenyihydrazone, 1-phenyl-1-ethanone 1,1-di(2-methoxyethyl)hydrazone, 1-[3-(dimethylamino)phenyl]-1-ethanone 1,1-diethylhydrazone, 2-[(Z)-2,2-diethylhydrazono]propyl cyanide, 2-[(E)-2-ethyl-2-phenylhydrazono]3-methoxypropyl cyanide, (Z)-1-chloro-1-penten-3-one 3-methyl-3-phenylhydrazone, 2-propynal 1-[4-(dimethylamino)phenyl]-1-methylhydrazone, ferrocenemethylketone-N,N-diphenylketone, 4-diethylaminobenzaldehyde-N,N-diphenylhydrazone, 4-diphenylaminobenzaldehyde-N,N-diphenylhydrazone, 9-ethylcarbazole-3-aldehyde-N,N-diphenylhydrazone, 9-ethylcarbazole-3-aldehyde-N-methyl-N-phenylhydrazone, and benzophenone-N,N-diphenylhydrazone; and radical cations of nickel oxide, iridium oxide, cerium oxide, vanadium pentoxide, niobium oxide, indium oxide, cobalt oxide, and molybdenum oxide, and mixtures of these oxides, Prussian blue, polyaniline, and polythiophene.

BRIEF DESCRIPTION OF THE DRAWINGS

The accompanying drawings, which are incorporated in and form a part of the specification, illustrate the embodiment(s) of the present invention and, together with the description, serve to explain the principles of the invention. In the drawings.

DETAILED DESCRIPTION

Figure 2:
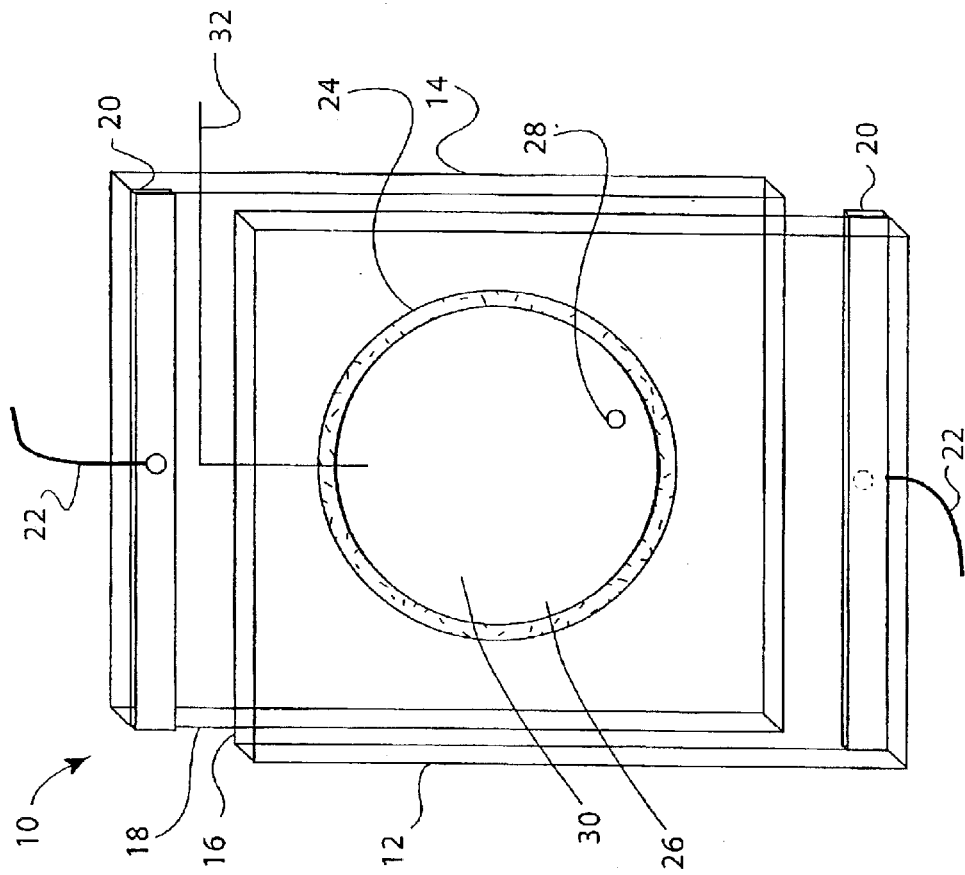
FIG. 2 shows a perspective view of the embodiment of the reversible electro-optic device of FIG. 1.

The invention includes a reversible electro-optic device that includes a substantially transparent chamber formed from a transparent working electrode, a counter electrode, and a gasket between the working electrode and counter electrode. Molten salt electrolyte in the chamber includes aprotic molten salt and soluble metal-containing ionic species that include metal that can be reversibly electrodeposited on the working electrode. An electric power source, such as a battery, power supply or a solar cell, drives the electrochemical reaction to deposit a thin layer of metal on the working electrode. Electro-optic devices include electrically-controlled mirrors, displays, variable transmittance windows, and other devices in which the optical properties are controlled electrically. Preferable electro-optic devices of the invention are devices that reflect light, i.e. reversible mirrors.

The aprotic molten salts used with the invention have the advantages of very low vapor pressure, low water content, low electrolyte resistance, and high metal ion solubility. They are very stable towards light, do not degrade seals, and include anions that are very difficult to oxidize or reduce. The reversible mirror of the invention employs these aprotic molten salts to overcome many of the disadvantages of known reversible mirrors.

A further advantage of molten salts relates to metal ion complexation. For reversible mirrors that employ aqueous electrolytes, water and hydroxide may participate as ligands that form bonds to metal ions. In most cases, metals without ligands are insoluble in organic solvents. An overpotential is required to electrodeposit a ligated metal (i.e. a metal having ligands attached to it) that exceeds the potential to electrodeposit an unligated metal by an amount equal to the potential required to break the bond between the metal and the ligand. By contrast, aprotic molten salts used with the invention do not form strong bonds to metal ions. Consequently, the overpotential required for electroplating metals from molten salts used with the invention is minimized.

Another advantage of molten salts relates to conductivity. Molten salts are more conductive than organic solvents because molten salts are ionic materials; ions are present in much higher concentrations in molten salts than in organic solvents. Tetraalkylammonium-based electrolytes, for example, are typically present in a concentration of 0.1 mol/L in organic solvents, but are present in a concentration in excess of 3 mol/L in molten salt electrolytes.

Still another advantage is that gases, such as hydrogen gas, are highly soluble in molten salts.

Preferred molten salts used with the invention are aprotic (i.e. do not contain dissociable hydrogen), very transparent to ultraviolet light and visible light, and provide devices that are operable at temperatures ranging from about −40° C. to about 120° C.

Preferred molten salts include cations selected from lithium cation (see, for example Kirk-Othmer's Encyclopedia of Chemical Technology, Fourth Edition, vol. 3, pp. 1016–1018 (1992) and pp. 1107–1109; and vol. 15, pp. 446–447 (1995) all incorporated by reference) and quaternary ammonium cations (see, for example, J. Sun et al., "Room Temperature Molten Salts Based on the Quaternary Ammonium Ion," J. Phys. Chem. B, 1998, vol. 102, pp. 8858–8864, incorporated by reference), and fluorine-containing anions.

Preferred quaternary ammonium cations include aprotic tetraalkylammonium, pyridinium, pyridazinium, pyrimidinium, pyrazinium, imidazolium, pyrazolium, thiazolium, oxazolium, and triazolium (see, for example, U.S. Pat. No. 5,827,602 to V. R. Koch et al. entitled "Hydrophobic Ionic Liquids," which issued Oct. 27, 1998, incorporated by reference herein). Tetraalkylammonium cations are most preferred because they have the least optical absorbance in the ultraviolet portion of the spectrum, which gives molten salts based on these cations enhanced photochemical stability. Most preferred cations are quaternary ammonium cations having the formula $(CH_3CH_2)_3N(R_1)$, wherein $R_1$ is alkyl having 2–10 carbons; or having the formula $(CH_3)_2(CH_3CHCH_3)N(R_2)$, wherein $R_2$ is alkyl having 2–10 carbons; or having the structural formula

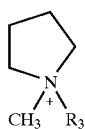

wherein $R_3$ is alkyl having 2–10 carbons;
or having the structural formula

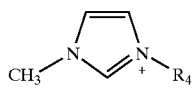

wherein $R_4$ is alkyl having 2–10 carbons.

Preferred fluorine-containing anions include trifluoromethylsulfonate $(CF_3SO_3^-)$, Bis(trifluoromethylsulfonyl)imide $((CF_3SO_2)_2N^-)$, bis(perfluoroethylsulfonyl)imide $((CF_3CF_2SO_2)_2N^-)$ and tris(trifluoromethylsulfonyl)methide $((CF_3SO_2)_3C^-)$. Bis(perfluoroethylsulfonyl)imide $((CF_3CF_2SO_2)_2N^-)$ anions are preferred because of their high hydrophobicity. Bis(trifluoromethylsulfonyl)imide anions are most preferred because of their low cost and high hydrophobicity. The bis(trifluoromethylsulfonyl)imide anion is sometimes referred to in the prior art as bis(trifluoromethanesulfonyl)amide or bis(trifluoromethanesulfonyl)imide. It has the structural formula

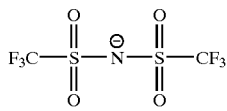

and is a poor ligand for most metals. A reversible mirror employing bis(trifluoromethylsulfonyl)imide allows metal electrodeposition (i.e. mirror formation) at a lower applied voltage than is needed for metal electrodeposition in aqueous or conventional organic solvent systems, or in molten salts in which strongly coordinating ligands (e.g. halides, pseudohalides, and the like) are present.

Most preferably, the aprotic molten salt is N-butyl-N-methylpyrrolidinium bis(trifluoromethylsulfonyl)imide.

Commercially available molten salts typically include colored impurities that cannot be removed by distillation. U.S. Pat. No. 5,827,602 to V. R. Koch et al. describes preparation of molten salt that includes purification of anion precursor using activated charcoal. One aspect of the present invention relates to an alternative preparation. According to the invention, and by contrast to Koch et al., the cation precursor is exposed to charcoal or activated carbon. Impure molten salt was prepared using the purified cation precursor and purified using activated alumina. Details related to the preparation of substantially pure molten salts are given in EXAMPLES 1 and 5–9 (vide infra).

Preferred metals that can be electrodeposited include aluminum, silicon, gallium, germanium, arsenic, selenium, indium, tin, antimony, tellurium, thallium, lead, bismuth, titanium, vanadium, chromium, manganese, iron, cobalt, nickel, copper, zinc, silver, gold, tungsten, lanthanum, cerium, praseodymium, neodymium, samarium, europium, gadolinium, terbium, dysprosium, holmium, erbium, thulium, yttrium, magnesium, calcium, lithium, and mixtures thereof. Main group metals are preferred because of their low cost and facile reduction. First row transition metals are preferred for their low cost. Lanthanides are preferred because of the appearance of the mirrors that they form. The metal ions must be in a form capable of being electrodeposited, such as in the form of metal ions. Metal ions can be introduced as dissolved ions. Alternatively, bulk metal may be introduced in the chamber of the device and then oxidized to form metal ions. Because the preferred anions do not coordinate strongly, ions of any metal may be electroplated.

As metal ions are reduced and electrodeposited, anodic materials are oxidized. Anodic materials often form radical cations when oxidized in the presence of anions. When an anodic material is oxidized to the corresponding radical cation in the presence of bis(trifluoromethylsulfonyl)imide, an ionic compound having bis(trifluoromethylsulfonyl)imide anion and the radical cation of the anodic material is formed. Anodic materials can be metal ions (e.g. bismuth (III) ions, iron (II) ions, and the like), organometallic compounds (e.g. ferrocene), or organic compounds (e.g. 9,10-dimethylphenazine). Many organic anodic compounds that are known to have the best electrochemical behavior are compounds that have two or more atoms with lone pairs of electrons (e.g. nitrogen, oxygen, sulfur, and the like), in which these atoms are chemically conjugated (i.e. connected by an even number of carbon atoms that have alternating double bonds). Examples include 1,2- and 1,4-disubstituted aryl compounds. Frequently, anodic materials become more intensely colored when they are oxidized.

Preferred anodic compounds include those having the structural formula

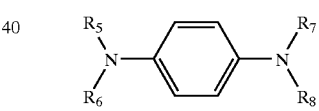

wherein $R_5$, $R_6$, $R_7$ and $R_8$ are the same or different and are each selected from hydrogen, alkyl of 1 to 10 carbon atoms, phenyl optionally substituted at any one position with chloride, bromide, iodide, cyano, or an alkyl group of 1 to 4 carbon atoms, and benzyl, wherein the phenyl moiety of the benzyl group is optionally substituted at any one position with chloride, bromide, iodide, cyano, or an alkyl group of 1 to 4 carbon atoms; or compounds having the structural formula

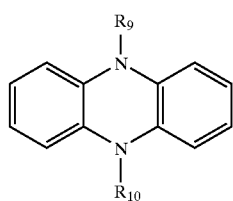

wherein $R_9$ is the same as or different from $R_{10}$ and both $R_9$ and $R_{10}$ are selected from alkyl of 1 to 10 carbon atoms, phenyl optionally substituted at any one position with chloride, bromide, iodide, cyano, or alkyl of 1 to 4 carbon atoms, or benzyl, optionally substituted at any one position of the phenyl group of the benzyl group with chloride, bromide, iodide, cyano, or alkyl of 1 to 4 carbon atoms; or compounds having the structural formula

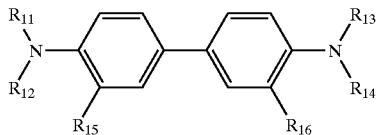

wherein $R_{11}$, $R_{12}$, $R_{13}$ and $R_{14}$ are the same or different and are each selected from alkyl of 1 to 10 carbon atoms or phenyl; and $R_{15}$ and $R_{16}$ are the same or different and are each selected from hydrogen or alkyl of 1 to 10 carbon atoms, provided that both $R_{15}$ and $R_{16}$ are hydrogen or both are alkyl, and if $R_{15}$ and $R_{16}$ are both hydrogen, not more than one of $R_{11}$ and $R_{12}$ is hydrogen and not more than one of $R_{13}$ and $R_{14}$ is hydrogen; or compounds having the structural formula

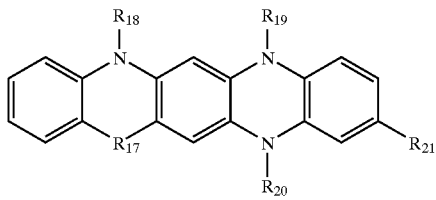

wherein $R_{17}$ is oxygen or sulfur, $R_{21}$ is hydrogen or dialkylamino, wherein the alkyl groups are the same or different and are each selected from alkyl of 1 to 6 carbon atoms, and $R_{18}$, $R_{19}$ and $R_{20}$ are the same or different and are each selected from hydrogen, alkyl of 1 to 6 carbon atoms, phenyl, optionally substituted at any one position with an alkyl group of 1 to 6 carbon atoms, and benzyl, optionally substituted at any one position of the phenyl group of the benzyl group with an
alkyl group of 1 to 6 carbon atoms; and or compounds having the structural formula

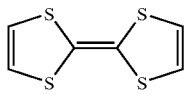

Other anodic compounds that may also be used with the invention are described in U.S. Patent Application 20030063365 to F. S. Wang et al. entitled "Electrochromic solution containing hydrazone compound and device manufactured with same," which was published Apr. 3, 2003, incorporated herein by reference. Wang describes the use of hydrazone-based anodic compounds in electrochemical cells. These hydrazones have the structural formula

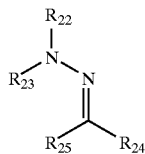

wherein $R_{22}$, $R_{23}$, $R_{24}$ and $R_{25}$ are individually selected from a group consisting of hydrogen, alkyl containing 5 to 20 carbon atoms, alkenyl containing 2 to 20 carbon atoms, alkynyl containing 2 to 20 carbon atoms, and aryl containing 5 to 20 carbon atoms which are unsubstituted or optionally substituted with one or more ester, ether, aryl, amine, thioester, alkyl, alkoxy, alkene, alkyne, cyano, fluoride, chloride, bromide, iodide, organometallocene functional groups, or combinations thereof.

In addition, acetone 2,2-dimethylhydrazone, 2-pentanone 2-ethyl-2-methylhydrazone, 2-ethylbutanal 1-ethyl-1-propylhydrazone, 2-ethyl-2-nonanone 2-hexyl-2-propylhydrazone, (E)-3-nonen-2-one 2-butyl-2-propylhydrazone, 2-hexanone 2-[(E)-2-butenyl]-2-[(Z)-2-butenyl]-hydrazone, 4-pentyn-2-one 2,2-dipropylhydrazone, 1-penten-3-one 3,3-dimethylhydrazone, 2-hexanone 2,2-diphenylhydrazone, 3heptanone 3-methyl-3-phenylhydrazone, 1-ethoxy-2-butanone 2-methyl-2-phenylhydrazone, 1-phenylacetone 2-(3methoxyphenyl)-2-phenylhydrazone, 2-phenacetaldehyde 1-methyl-1-phenylhydrazone, methyl 3-[(Z)-2-methyl-2-phenylhydrazone]-butanethioate, 1-(3-chlorophenyl)-3-methoxy-1-propanone 1-methyl-1-(3-methylphenyl) hydrazone, ferrocenephenylketone 2-[(E)-2-butenyl]-2-[(Z)-2-butenyl]hydrazone, bis(cyclopentadienyl) cobaltmethylketone 2,2-diphenylhydrazone, bis (cyclopentadienyl)dimethylzirconiummethylketone 2,2-diphenyihydrazone, 1-phenyl-1-ethanone 1,1-di(2-methoxyethyl)hydrazone, 1-[3-(dimethylamino)phenyl]-1-ethanone 1,1-diethylhydrazone, 2-[(Z)-2,2-diethylhydrazono]propyl cyanide, 2-[(E)-2-ethyl-2-phenylhydrazono]-3-methoxypropyl cyanide, (Z)-1-chloro-1-penten-3-one 3-methyl-3-phenylhydrazone, 2-propynal 1-[4-(dimethylamino)phenyl]-1-methylhydrazone, ferrocenemethylketone-N,N-diphenylketone, 4-diethylaminobenzaldehyde-N,N-diphenylhydrazone, 4-diphenylaminobenzaldehyde-N,N-diphenylhydrazone, 9-ethylcarbazole-3-aldehyde-N,N-diphenylhydrazone, 9-ethylcarbazole-3-aldehyde-N-methyl-N-phenylhydrazone, and benzophenone-N,N-diphenylhydrazone may also be used as anodic compounds in the present invention.

Solid-state anodic compounds may also be used with the present invention. Solid-state anodic compounds are described in U.S. Pat. No. 5,663,829 to C. Lefrou et al. entitled "Electrochromic pane," which issued Sep. 2, 1997, incorporated herein by reference; and U.S. Pat. No. 5,404, 244 to J. Van Dine et al. entitled "Electrochromic structures and methods," which issued Apr. 4, 1995, incorporated herein by reference. Solid-state anodic compounds include low valent metal oxides, i.e. metal oxides that are not in their highest oxidation state and that may therefore by oxidized, such as nickel oxide, iridium oxide, cerium oxide, vanadium pentoxide, niobium oxide, indium oxide, cobalt oxide, and molybdenum oxide, and mixtures of these oxides; solid-state anodic compounds also include low valent metal compounds other than oxides, such as Prussian blue; and organic films, such as polyaniline, polythiophene, and other conducting polymers.

Preferred optically transparent electrodes include an optically transparent conducting oxide (e.g. indium tin oxide or fluorine-doped indium tin oxide) layered on a glass or plastic substrate.

Metal ion electrodeposition is achieved by application of a suitable potential difference across the working electrode and the counter electrode so that the working electrode has an electric potential equal to or more negative than that required to achieve reduction of the metal ion in the electrolyte solution to the zero oxidation state. Simultaneously at the counter electrode, an equal amount of electrical charge is associated with oxidation of anodic materials from the solution.

The quantity of metal deposited on the working electrode affects the opacity of the mirror formed, and can be monitored by measuring the quantity of the electric current used to deposit metal on the working electrode. The mirror opacity can range from partially reflective and partially transparent to completely reflective and completely opaque. The quantity of metal deposited on the working electrode is controlled by the electric potential of the working electrode and the time for which this electric potential is applied.

The reversal of electrodeposition, i.e. mirror dissolution, is performed by applying a potential difference across the device so that the working electrode has an electric potential equal to or more positive than that required to return the metal located on this working electrode to the oxidation state of those metal ions contained in the electrolyte solution. Simultaneously at the counter electrode, an equal amount of electrical charge is associated with reduction of the species formed at the counter electrode during metal electrodeposition so that the original species in the electrolyte is reformed. An alternative mechanism of mirror dissolution occurs when oxidized species diffuse from the counter electrode to the mirror phase, followed by oxidation of the mirror phase by the oxidized species.

The rate of metal electrodeposition, and hence rate of change in mirror thickness, may in part be controlled by the excursion of the electric potential of the working electrode in the negative direction away from the equilibrium potential for the metal ion in the electrolyte solution given by the well-known Nernst equation (see, for example, Physical Chemistry by Ira N. Levine, second edition, McGraw Hill Company, pp. 389–392, 395). This excursion in electric potential of the working electrode away from the equilibrium potential is widely known as the overpotential, $\eta$, which is given by the following equation $$\eta = E - E_{eq}$$

where E in this case is the electric potential of the working electrode with respect to a reference electrode potential and $E_{eq}$ is the equilibrium potential with respect to the same reference electrode for the metal ion in the electrolyte system as given by the Nernst equation. The equilibrium potential $E_{eq}$ is determined by the standard reduction potential, metal ion concentration and the operating temperature. In the present case, metal electrodeposition occurs at negative values of the overpotential.

In many electrochemical processes the rate of electron transfer to or from the working electrode to a species present in the solution is rate limiting. The rate of reaction often changes exponentially with linear changes in the overpotential and we anticipate that the rate of metal electrodeposition and hence mirror opacity at the working electrode grows exponentially for linearly more negative overpotentials. This exponential increase in metal electrodeposition rate with increasingly more negative overpotential may prevail until either diffusion-controlled mass-transport of the metal ion from the bulk electrolyte solution to the working electrode-electrolyte interface, or nucleation and growth phenomenon, limit the overall process. It should be noted that at a fixed negative overpotential, the rate of metal electrodeposition and hence changes in mirror opacity at the working electrode are not expected to remain constant as a function of time because the relative control by either diffusion control or nucleation and growth may change as a function of time in a complicated and inter-related manner.

The extent of metal electrodeposition rate-limitation by diffusion control may be mitigated by a number of factors including: metal ion concentration in the electrolyte solution; extent of metal-ion complexation in the electrolyte; electrolyte viscosity; and temperature. According to Fick's First Law of Diffusion (see, for example, Physical Chemistry by Ira N. Levine, second edition, McGraw Hill Company, page 465), an increase in the bulk concentration of the metal ion in the electrolyte will permit a linear increase in the rate of diffusion. In a reversible mirror device two scenarios may be envisaged with respect to metal ion concentration. The first scenario is that only sufficient metal ions are present in the electrolyte solution so that complete electrodeposition of all these ions as zero oxidation state metal at the working electrode achieves the desired level of mirror opacity for the device. Here, the diffusion-controlled rate of metal electrodeposition will continually decline with time as the bulk concentration of the metal ion decreases to zero. Complete electrodeposition thus requires extended periods of time. In the second scenario the concentration of the metal ion in the electrolyte is sufficiently high that removal of the quantity of metal ions from this solution to affect the desired mirror thickness does not significantly alter the bulk metal ion concentration. Consequently, the diffusion-limiting rate does not vary during electrodeposition and may be maintained at a high rate.

Fick's First Law also states that increasing the diffusion coefficient will also afford a linear increase in the rate of diffusion. The diffusion coefficient may be described by the Stokes-Einstein relationship (see, for example, Physical Chemistry by Ira N. Levine, second edition, McGraw Hill Company, page 471). According to this relationship, the diffusion coefficient and hence rate of metal electrodeposition is expected to increase with lower viscosity electrolytes, higher increasing temperatures, and smaller diffusing species.

Ensuring that the smallest metal-containing species moves to the working electrode is a challenge. Metal ions are generally surrounded by solvent molecules and/or by other ligands. If large ligands bind to the metal ion center, then the diffusing species will be large and the mass-transport limiting rate for metal electrodeposition will be low. Conversely, if the ligands are small, then fast diffusing species may form. However, the strength of the binding between the metal ion center and the solvent or ligand molecules can influence the overpotential for metal electrodeposition. If solvent or ligand molecules are tightly bound to the metal ion center, then a larger overpotential may be required to achieve a given metal electrodeposition rate even under electron-transfer control compared to a less tightly bound metal ion species.

The control of metal electrodeposition by nucleation and growth phenomenon may be influenced by deliberate supply of nucleation sites on the working electrode surface. Here, either thin layers or discrete small islands of a metal (preferably a noble metal such as platinum) may be deposited onto the working electrode prior to assembly of the reversible mirror device. This may achieved by a number of techniques, including, but not limited to electrochemical deposition, chemical vapor deposition and arc sputtering. The quantity of the metal is sufficiently small that the working electrode retains optically transparency. The metal nuclei result in the removal or decrease in the initial overpotential required for formation of the first nuclei of a depositing metal on an electrode surface devoid of that metal. A further advantage in employing discrete islands of metal nuclei is that the relative dispersion of the subsequent metal electrodeposition is pre-defined. This metal deposition should not decrease the absolute transmission of light of the substrate by more than 30%. A more preferred decrease is less than 15%. This decrease may be measured at any desired wavelength, however for optical devices in visible range a convenient wavelength is 550 nm.

The rate at which electrodeposited metal is removed from the working electrode is also affected by the aforementioned features of electron-transfer and mass-transport.

The above factors affecting electron transfer and mass transport for metal electrodeposition at the working electrode also apply to the oxidation processes at the counter electrode. Thus, an exponential increase in oxidation rate at the counter electrode occurs from linear increases in the positive overpotential for the solution species until mass transport processes limit the overall rate. In general, if the product of oxidation at the counter electrode is soluble in the electrolyte solution, then it is desirable that this product is present in concentrations sufficient to ensure that diffusion of this oxidized species to the counter electrode during reversal of mirror electrodeposition does not limit the performance of the reversible mirror device. If, however, the oxidized species formed at the counter electrode during mirror formation deposits on the counter electrode and is electrochemically accessible during reversal of mirror formation, then there is no need for this species to be in solution.

In reversible mirror devices, the potential difference across the device, $E_{mirror}$ is defined in the equation below:

$$E_{mirror} = (\eta_{CE} - E_{eq,CE}) - (\eta_{WE} - E_{eq,WE}) - IR$$

where $\eta_{CE}$ and $\eta_{WE}$ are the overpotentials for the counter and working electrodes respectively, and $E_{eq,CE}$ and $E_{eq,WE}$ are the equilibrium potentials for the counter and working electrodes respectively, and IR drop is the effective loss of potential difference due to the flow of current, I, through a resistance R. The current I is the current that flows through the device due to electrodeposition or its reverse, and is a function of time, potential difference, species concentration and temperature. The resistance is due to the effective resistance of the electrolyte solution arising from conductivity of the solution. In some cases the IR drop is appreciable when compared to the potential difference across an electrochemical device. Consequently, it is preferable to employ highly conductive charged species in the electrolyte to minimize IR drop. In aqueous solutions this is achieved by addition of high concentrations of high conductivity salts such as potassium nitrate or potassium chloride. In organic solvents, metal salts such as these are not sufficiently soluble. Instead, significantly less conductive, but more soluble, salts of tetraalkylammonium cations are employed.

The invention employs molten salt electrolytes, which are more conductive than organic solvents because molten salts are ionic materials; ions are present in much higher concentrations in molten salts than in organic solvents. Tetraalkylammonium-based electrolytes, for example, are typically present in a concentration of 0.1 mol/L in organic solvents. By contrast, they are present in a concentration in excess of 3 mol/L in molten salt electrolytes.

The electrodeposition of metal on the working electrode may or may not result in the formation of a reflective mirror or optical opacity in the visible region of the electromagnetic spectrum. The extent of reflectance or opacity at the working electrode depends on the quantity of metal deposited, the distribution of nucleation sites and the consequent distribution of metal across the device, the adhesion of the metal to the transparent working electrode, and the shape of the metal deposit (e.g. smooth layers versus dendritic metal crystallites). All these factors will influence the visible light scattering properties of the deposited metal.

The counter electrode may participate in determining the optical appearance and opacity of the reversible mirror device. If the oxidation product formed at the working electrode and the solution precursor are soluble and colorless, then the optical appearance of the reversible mirror will be determined entirely by the working electrode.

If the oxidation products or the precursors are soluble and colored, then reflectance or optical opacity at the working electrode will be accompanied by a color change when viewed from the counter electrode side. The oxidation product at the counter electrode may alternatively form a solid layer that adheres to the counter electrode; this layer could be colored or optically opaque. Combinations of the reflectance or opacity at the working electrode, colors and solubilities of the species involved in the counter electrode reactions, and viewing direction through the reversible mirror lead to numerous possibilities for the optical appearance of the device. Devices with variable transmission made according to the invention will have a transmission of greater than 20% in the bleached state, and more preferably greater than 50% at 550 nm. In the reflective state, their transmission will be less than 15% and more preferably less than 5%. For windows offering privacy, transmission in the reflective state will be preferably lower than 0.1%.

Figure 1:
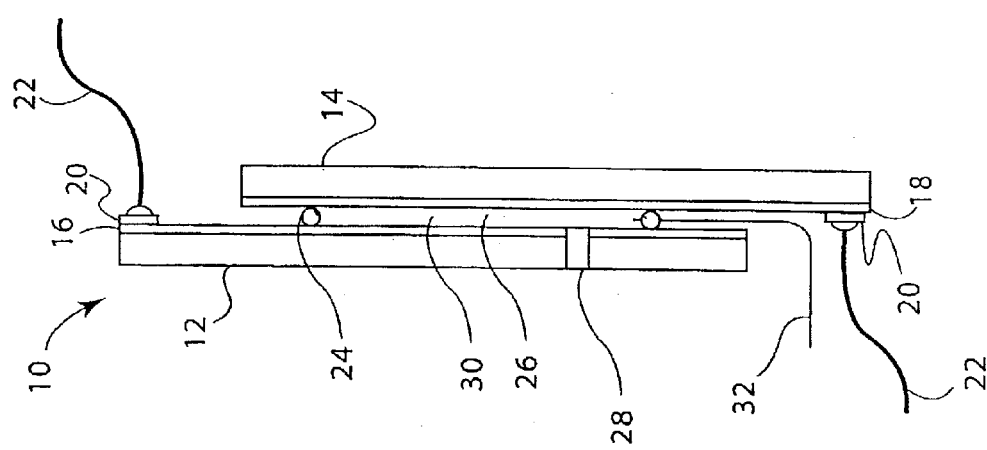
FIG. 1 shows a cutaway, edge-on view of an embodiment of the reversible electro-optic device of the invention.

Reference will now be made in detail to the present preferred embodiments of the invention. Similar or identical structure is identified using identical callouts. FIG. 1 shows an edge-on view of an embodiment of a reversible mirror of the invention. FIG. 2 shows a perspective view of the embodiment of FIG. 1. Reversible mirror 10 includes first substrate 12 and second substrate 14. For convenience, small flat pieces of glass were employed as substrates. It should be understood that the substrates are not limited to any particular shape or material, such as plastic, or glass, and that one electrode may be made of an opaque substrate such as metal or metal-coated plastic or metal-coated glass. Curved substrates, for example, may also be used. The substrates may be roughened to reduce reflection of radiation from the electrode or to improve the kinetics of the electrodeposition because roughening the surface increases the surface area and lowers the current density. First conductive layer 16 is on a face of first substrate 12 and optional second conductive layer 18 is on a face of second substrate 14. Conductive layers are typically indium tin oxide, or fluorine-doped indium tin oxide, but any conductive coating, such as thin layers of metal or films of conducting polymers may be used. Conductive layers may be optionally modified with either a thin film, mesh, pattern, or random discrete islands of noble metal such as platinum, iridium, gold, osmium, palladium, rhenium, rhodium and ruthenium, or alloys thereof which act as nucleation centers for metal electrodeposition. The conductive layer, with or without the optional noble metal modification, forms the working electrode. This modification may be done by any known methods; some of these are physical vapor deposition (evaporation and sputtering), chemical vapor deposition or electro-deposition. Optional conductive layer 18 is needed if second substrate 14 is not conductive, for example if second substrate 14 is made of glass or plastic. Optional conductive layer 18 is not needed if second substrate 14 is conductive, for example if second substrate 14 is made of metal or metal-coated glass or metal coated plastic. In the event that second substrate 14 is conductive, then second substrate 14 functions as both structural substrate and conductive layer. Reversible mirror 10 includes metallic bus bars 20. One bus bar 20 is attached to an end portion of first conductive layer 16. Another bus bar 20 is attached to an end portion of second conductive layer 18. If second substrate 14 is electrically conductive, then the bus bar 20 may be directly attached to second substrate 14. Bus bars 20 are made from suitable conductive metallic material and provide good electrical contact to the conductive layers or the substrate. Examples of bus bar materials are silver frits, solder alloys, metallic strips, wires and clips. Preferred materials include copper, copper alloys (such as copper-beryllium alloys), and tin plated copper. A wire 22 is soldered or otherwise attached to each bus bar 20 for connecting to a voltage source (a battery or the like, not shown). Reversible mirror 10 includes electrically non-conductive gasket 24. Gasket 24 forms a seal with first conductive layer 16 and with second conductive layer 18, or with second substrate 14 if second conductive layer 18 is not used, to provide chamber 26. Preferably, the chamber width between the substrates is from about 30 microns to about 5000 microns. More preferably, the chamber width is from about 40 microns to about 500 microns.

Gasket 24 should be chemically stable to molten salt electrolyte used with the invention, substantially impermeable to water and the atmosphere (especially to oxygen and carbon dioxide), and robust over a wide temperature range, preferably from about −80° C. to about 150° C. Gasket 24 provides electrical insulation between the two conducting surfaces so that substantially all electrical current passes through the solution 30. The thickness of gasket 24 determines the distance between the first conductive layer 16 (i.e. the working electrode) and second conductive layer 18 (i.e. the counter electrode), and affects the volume of chamber 26 and internal resistance of device 10. Optionally, a small volume of gas may be included within chamber 26 to mitigate expansion and contraction.

Device 10 includes at least one port 28 for filling chamber 26 with solution 30 of molten salt electrolyte and metal ions dissolved therein. Port 28 may be located at any convenient location (through gasket 24, through first substrate 12, through second substrate 14, for example). Only one port is needed if vacuum-backfill techniques are used to fill chamber 26 with solution 30, but additional ports, for the purpose of e.g. pressure relief, may be present if different fill methods are used. After filling chamber 26, port(s) 28 are plugged.

The molten salt electrolyte is non-volatile and hydrophobic, and provides high concentrations of cations and anions that offer minimal resistance to current. Solution 30 in chamber 26 remains in electrical contact with first conductive layer 16 and second conductive layer 18 (or with second substrate 14 if second conductive layer 18 is not used). Solution 30 includes metal ions capable of being electrochemically reduced to the zero oxidation state and electrodeposited on first conductive layer 16 (and on optional noble metal islands). Ions of a single metal or of a combination of two or more metals may be present in the electrolyte so that one, or two or more metals may be deposited either simultaneously or in some sequence, either as an alloy or alloys, or as layers or as discrete islands of metals on first conductive layer 16 (i.e. the working electrode).

Device 10 also includes anodic materials. Anodic materials are either dissolved in solution 30 or present as a solid on second conductive layer 18, which functions as a counter electrode. Anodic materials may be optionally colored in either the oxidized or the reduced state. The anodic materials oxidized during electrodeposition may form a solid layer on conductive layer 18.

The bulk of solution 30 is aprotic molten salt. The cation of the molten salt is preferably a tetraalkylammonium, alkyl-substituted pyrrolidine, or alkyl-substituted imidazole. The anion of the molten salt is preferably perchlorate, tetrafluorborate, hexafluorophosphate and trifluoromethyl-sulfonate ($CF_3SO_3^-$), bis(trifluoromethylsulfonyl)imide (($CF_3SO_2)_2N^-$), bis(perfluoroethylsulfonyl)imide (($CF_3CF_2SO_2)_2N^-$) and tris(trifluoromethylsulfonyl) methide (($CF_3SO_2)_3C^-$).

Most preferably, the aprotic molten salt is N-butyl-N-methylpyrrolidinium bis(trifluoromethylsulfonyl)imide.

Solution 30 may optionally contain thixotropic agents, such as dispersed, electrochemically inert inorganic materials such as silica or alumina to facilitate injection into chamber 26.

Solution 30 may also contain one or more coloring agents to afford a desired color in either the mirrored state of the apparatus or the non-mirrored state of the apparatus.

Solution 30 may also contain soluble ultraviolet (UV) stabilizers that stabilize the anodic materials against degradation from UV light. Examples of UV stabilizers can be found in: Modern Plastics World Encyclopedia (2001) p-C-120 to C-122, Chemical Week Publishing, NY, incorporated by reference herein.

Solution 30 may also contain one or more stiffening agents to increase the viscosity of solution 30 while maintaining conductivity. This is desirable in order to minimize the spread of solution 30 if device 10 is damaged. Stiffening agents include, but are not limited to, organic monomers and polymers such as polyacrylonitrile, polyvinlidene fluoride, hexafluoropropylene, polyvinyl alcohol, polyvinylacetate, polymethylmethacrylate and their copolymers. These polymers may be formed in situ. They may be crosslinked in situ by polymerization of monomers (see, for example, U.S. Pat. No. 6,420,036 to D. V. Varaprasad et al. entitled "Electrochromic Polymeric Solid Films, Manufacturing Electrochromic Devices Using Such Solid Films, and Processes for Making Such Solid Films and Devices," incorporated by reference herein). Poly(methylmethylacrylate) (PMMA), for example, may be formed by adding methyl methylacrylate to the molten salt and then adding benzoyl peroxide to initiate the polymerization.

Solution 30 optionally includes one or more soluble co-solvents that decrease the viscosity of solution 30 and do not interfere with the durability and function of the reversible mirror. Preferably, co-solvents are aprotic and have high boiling points (i.e. above 150° C.), low melting points (i.e. below −30° C.), and are present in concentrations of about 0.5% to 30%. Preferable co-solvents include propylene carbonate, N-methyl pyrrolidinone, perfluorodecalin, and perfluorodecane.

Optionally, device 10 may include pseudo-reference electrode 32 for evaluating the electric potential of conductive layer 16. Pseudo-reference electrode 32 may be in the form of a silver wire inserted through gasket 24 such that pseudo reference electrode 32 does not contact conductive layer 16 or conductive layer 18. Pseudo-reference electrodes may take other forms. A minor portion of first conductive layer 16 or second conductive layer 18 may be separated away by etching a separation line to provide a pseudo-reference electrode.

The invention can be used with a standard, glass, multiple-pane window by substituting a pane of the multi-pane window with the reversible mirror of the invention. The other glass panes of the multiple-pane window may be coated with low-emissivity materials that block UV, infrared, and/or visible light.

The invention is further illustrated by the following EXAMPLES. EXAMPLES 1–4 provide details for fabricating working embodiments of the reversible mirror of the invention. EXAMPLES 1 and 5–9 include procedures for preparing substantially pure molten salts that can be used with the invention.

EXAMPLE 1

An embodiment of a reversible mirror of the invention was fabricated as follows: two electrodes were prepared using 6×8 cm single-side planar ITO coated glass plates having a sheet resistivity of 7Ω/square. Each plate was provided with a bus bar by attaching a copper electrical contact approximately 1 cm wide along the entire edge of the 6 cm end of each plate. The electrodes were then washed with water, methanol and acetone, and dried in a stream of warm air to remove any dust or grease.

An o-ring (2 cm internal diameter (ID) vycor rubber donut-shaped o-ring, 0.3 cm thick) was used as a gasket to seal one electrode to the other. A silver wire (5 cm long, 0.25 mm diameter, 99.9% metal purity) was inserted through the o-ring by first piercing a hollow needle through the o-ring, placing one end of the silver wire through the hollow needle, and then withdrawing the hollow needle from the o-ring. Approximately 0.4 mm of the silver wire protruded through the o-ring. The o-ring was then placed between the two electrodes with the conducting ITO coating in contact with the o-ring (see FIGS. 1 and 2) with the bus bars at opposite ends of the device. Two spring-loaded clips were used to hold the device together and provide a tight seal. A digital ohmmeter was used to ensure that the three electrodes (working, counter and pseudo-reference electrodes) were in electrical isolation of each other.

Butylmethylimidazolium bis(trifluoromethylsulfonyl) imide was synthesized as follows: Butylmethylimidazolium bromide (50 g) was dissolved deionized water (100 mL). Decolorizing charcoal or activated carbon (3 g) was added to the solution, which was boiled for 3 minutes and filtered. The filtrate was added to a solution of lithium bis (trifluoromethylsulfonyl)imide (65.5 g) in 100 mL of deionized water. After stirring at room temperature for 3 hrs, two layers formed. The bottom layer containing butylmethylimidazolium bis(trifluoromethylsulfonyl)imide was separated, washed deionized water (3×50 mL), heated at 100 ° C. under vacuum (0.1 mbar) for 48 hrs, and then filtered through activated alumina to give anhydrous, highly pure, molten butylmethylimidazolium bis(trifluoromethylsulfonyl)imide. The purity of the molten salt was assayed by cyclic voltammetry, absorbance spectroscopy or fluorescence measurements.

A solution of 3-butyl-1methylimadazolium bis (trifluoromethylsulfonyl)imide containing less than 1 ppm water and 0.035 mol/L of bismuth (III) bis (trifluoromethylsulfonyl)imide was prepared in a helium atmosphere drybox. The solution was introduced into the chamber of the device by inserting two hollow needles through the o-ring (one needle for introducing the solution, the other needle for removing displaced gas). Afterward, the needles were removed and the o-ring was checked for leaks. Wire connectors were attached to the bus bars and to a potentiostat that provided the voltage for electrodeposition. A bismuth mirror was deposited at a potential of −0.65 Volts versus the silver reference electrode. The bismuth mirror was deplated at a potential of +0.1 Volts versus the silver reference electrode. Overall, this reversible mirror device exhibited good optical reflectance in the reflective state and good transparency in the non-mirrored state, and was switched repetitively between these two states without degradation of performance.

EXAMPLE 2

A second working embodiment of a reversible mirror of the invention was fabricated using the general procedure provided in EXAMPLE 1 but with a solution of 3-butyl-1-methylimadazolium bis(trifluoromethylsulfonyl)imide (also containing less than 1 ppm water) and 0.792 mol/L of iron (II) is(trifluoromethylsulfonyl)imide. An iron mirror was deposited at a potential of −1.2 Volts versus the silver reference electrode. Twenty minutes after the potential was removed, the iron mirror deplated spontaneously. Overall, this reversible mirror device exhibited good optical reflectance in the reflective state and good transparency in the non-mirrored state, and was switched repetitively between these two states without degradation of performance.

EXAMPLE 3

A third working embodiment of a reversible mirror of the invention was fabricated using the general procedure provided in EXAMPLE 1 but with a solution of solution of 3-butyl-1-methylimadazolium bis(trifluoromethylsulfonyl) imide containing less than 1 ppm water and 0.073 mol/L ferrocene was used. By contrast to EXAMPLE 2, the iron is initially present as ferrocene. An iron mirror was initially deposited at a potential of −1.5 Volts versus the silver reference electrode. This iron mirror was deplated at a potential of +0.4 Volts versus the silver reference electrode and redeposited at a potential of −1.2 Volts versus the silver reference electrode. Overall, this reversible mirror device exhibited good optical reflectance in the reflective state and good transparency in the non-mirrored state, and was switched repetitively between these two states without degradation of performance.

EXAMPLE 4

A fourth working embodiment of a reversible mirror of the invention was fabricated using the general procedure provided in EXAMPLE 1 but with a solution of 3-butyl-1-methylimadazolium bis(trifluoromethylsulfonyl)imide containing less than 1 ppm water and 0.075 mol/L of zinc (II) bis(trifluoromethylsulfonyl)imide was used. A zinc mirror was deposited at a potential of −1.8 Volts versus the silver reference electrode. The zinc mirror was deplated at a potential of +0.5 Volts versus the silver reference electrode. Overall, this reversible mirror device exhibited good optical reflectance in the reflective state and good transparency in the non-mirrored state, and could be switched repetitively between these two states.

EXAMPLE 5

Butylmethylpyrrolidinium bis(trifluoromethylsulfonyl) imide was synthesized as follows: A solution of butylmethylpyrrolidinium bromide (500 g) in deionized water (1 L) was added to a solution of lithium bis (trifluoromethylsulfonyl)imide (646 g) in 1 L of deionized water. The resulting solution was stirred at room temperature for 3 hrs, after which two layers had formed. The bottom layer containing butylmethylpyrrolidinium bis (trifluoromethylsulfonyl)imide was separated, washed with deionized water (3×500 mL), and then heated at 100° C. under vacuum (0.1 mbar) for 48 hrs. Decolorizing charcoal or activated carbon (30 g) and activated alumina (100 g) were added to the molten salt. After stirring for 1 hr, the solids were removed by filtration. The purity of the molten salt was assayed by cyclic voltammetry, absorbance spectroscopy or fluorescence measurements. The treatment with charcoal or activated carbon and activated alumina may be repeated until the desired purity is obtained.

EXAMPLE 6

Butylmethylpyrrolidinium bis(trifluoromethylsulfonyl)imide was prepared as follows: decolorizing charcoal or activated carbon (30 g) was added to a solution of butylmethylpyrrolidinium bromide (500 g) in deionized water (1 L). The resulting mixture was boiled for three minutes, then cooled to room temperature and filtered. The filtrate (a purified solution of butylmethylpyrrolidinium bromide) was added to a solution of lithium bis(trifluoromethylsulfonyl)imide (646 g) in 1 L of deionized water, stirred at room temperature for 3 hrs, after which two layers had formed. The bottom layer containing butylmethylpyrrolidinium bis(trifluoromethylsulfonyl)imide was separated, washed with deionized water (3×500 mL), heated at 100° C. under vacuum (0.1 mbar) for 48 hrs, and then filtered through activated alumina to give the highly pure molten salt. The purity of the molten salt was confirmed by cyclic voltammetry, absorbance spectroscopy, or fluorescence measurements. This preparative method is preferred because it provides highly pure molten salt in high yield.

EXAMPLE 7

Butylmethylimidazolium bis(trifluoromethylsulfonyl)imide was synthesized as follows: A solution of butylmethylpyrrolidinium bromide (50 g) in deionized water (100 mL) was added to a solution of lithium bis(trifluoromethylsulfonyl)imide (65.5 g) in 100 mL of deionized water. The resulting solution was stirred at room temperature for 3 hrs, after which two layers had formed. The bottom layer containing butylmethylpyrrolidinium bis(trifluoromethylsulfonyl)imide was separated, washed with deionized water (3×50 mL), and then heated at 100° C. under vacuum (0.1 mbar) for 48 hrs. Decolorizing charcoal or activated carbon (3 g) and activated alumina (10 g) were added to the molten salt. After stirring for 1 hr, the solids were removed by filtration. The purity of the molten salt was assayed by cyclic voltammetry, absorbance spectroscopy or fluorescence measurements. The treatment with charcoal or activated carbon and activated alumina may be repeated until the desired purity is obtained.

EXAMPLE 8

Butylmethylimidazolium bis(trifluoromethylsulfonyl)imide was synthesized as follows: A solution of butylmethylpyrrolidinium chloride (40 g) in deionized water (100 mL) was added to a solution of lithium bis(trifluoromethylsulfonyl)imide (65.5 g) in 100 mL of deionized water. The resulting solution was stirred at room temperature for 3 hrs, after which two layers had formed. The bottom layer containing butylmethylpyrrolidinium bis(trifluoromethylsulfonyl)imide was separated, washed with deionized water (3×50 mL), and then heated at 100° C. under vacuum (0.1 mbar) for 48 hrs. Decolorizing charcoal or activated carbon (3 g) and activated alumina (10 g) were added to the molten salt. After stirring for 1 hr, the solids were removed by filtration. The purity of the molten salt was assayed by cyclic voltammetry, absorbance spectroscopy or fluorescence measurements. The treatment with charcoal or activated carbon and activated alumina may be repeated until the desired purity is obtained.

EXAMPLE 9

Butylmethylimidazolium bis(trifluoromethylsulfonyl)imide was synthesized as follows: Butylmethylimidazolium chloride (40 g) was dissolved deionized water (100 mL). Decolorizing charcoal or activated carbon (3 g) was added to the solution, which was boiled for 3 minutes and filtered. The filtrate was added to a solution of lithium bis(trifluoromethylsulfonyl)imide (65.5 g) in 100 mL of deionized water. After stirring at room temperature for 3 hrs, two layers formed. The bottom layer containing butylmethylimidazolium bis(trifluoromethylsulfonyl)imide was separated, washed deionized water (3×50 mL), heated at 100 ° C. under vacuum for 48 hrs, and then filtered through activated alumina to give anhydrous, highly pure, molten butylmethylimidazolium bis(trifluoromethylsulfonyl)imide. The purity of the molten salt was assayed by cyclic voltammetry, absorbance spectroscopy or fluorescence measurements.

The foregoing description of the invention has been presented for purposes of illustration and description and is not intended to be exhaustive or to limit the invention to the precise form disclosed, and obviously many modifications and variations are possible in light of the above teaching.

The embodiment(s) were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A reversible electro-optic device that comprises a chamber and, as the medium of variable transmittance to light, a solution of aprotic molten salt, at least one soluble metal-containing species comprising metal capable of being electrodeposited, and at least one anodic compound capable of being oxidized, wherein said solution of aprotic molten comprises anions, wherein said anions of said solution of aprotic molten salt do not bind strongly enough to said metal-containing species to form metal complexes with said anions.

2. The device of claim 1, wherein said aprotic molten salt is liquid at room temperature and comprises at least one cation selected from group consisting of lithium cation and quaternary ammonium cations, and at least one anion selected from the group consisting of trifluoromethylsulfonate ($CF_3SO_3^-$), bis(trifluoromethylsulfonyl)imide (($CF_3SO_2)_2N^-$), bis(perfluoroethylsulfonyl)imide (($CF_3CF_2SO_2)_2N^-$) and tris(trifluoromethylsulfonyl)methide (($CF_3SO_2)_3C^-$).

3. The device of claim 2, wherein said quaternary ammonium cations are selected from the group consisting of pyridinium, pyridazinium, pyrimidinium, pyrazinium, imidazolium, pyrazolium, thiazolium, oxazolium, triazolium, tetraalkylammonium, and N-methyl morpholinium cations.

4. The device of claim 2, wherein said quaternary ammonium cations comprise the formula $[(CH_3CH_2)_3N(R_1)]^+$, wherein $R_1$ is alkyl having 2–10 carbons; or comprise the formula $[(CH_3)_2(CH_3CHCH_3)N(R_2)]^+$, wherein $R_2$ is alkyl having 2–10 carbons; or comprise the structural formula

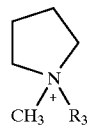

wherein $R_3$ is alkyl having 2–10 carbons;

or comprise the structural formula

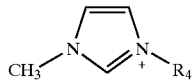

wherein $R_4$ is alkyl having 2–10 carbons.

5. The device of claim 2, wherein said molten salt comprises butylmethylpyrrolidinium bis(trifluoromethylsulfonyl)imide.

6. The device of claim 1, wherein said reversible electro-optic device comprises a reversible mirror.

7. The device of claim 1, wherein said metal-containing species comprises metal selected from the group consisting of aluminum, silicon, gallium, germanium, arsenic, selenium, indium, tin, antimony, tellurium, thallium, lead, bismuth, titanium, vanadium, chromium, manganese, iron, cobalt, nickel, copper, zinc, silver, gold, tungsten, lanthanum, cerium, praseodymium, neodymium, samarium, europium, gadolinium, terbium, dysprosium, holmium, erbium, thulium, yttrium, magnesium, calcium, lithium, and mixtures thereof.

8. The device of claim 1, wherein said metal-containing species comprises a concentration of from about 0.01 moles per liter to about 1 mole per liter.

9. The device of claim 1, wherein said anodic compound comprises iron (II) salts, iron (II) organometallic compounds, bismuth (III) salts, nickel oxide, iridium oxide, cerium oxide, vanadium pentoxide, niobium oxide, indium oxide, cobalt oxide, and molybdenum oxide, and mixtures of these oxides, Prussian blue, polyaniline, polythiophene, and organic compounds that, in a voltammogram done in the solvent at room temperature, display at least two chemically reversible oxidations, with the first of said oxidations accompanied by an increase in molar extinction coefficient at at least one wavelength in the visible range.

10. The device of claim 1, wherein said anodic compound is selected from the group consisting of compounds comprising the structural formula

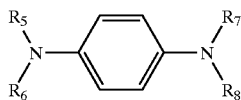

wherein $R_5$, $R_6$, $R_7$ and $R_8$ are the same or different and are each selected from hydrogen, alkyl of 1 to 10 carbon atoms, phenyl optionally substituted at any one position with chloride, bromide, iodide, cyano, or an alkyl group of 1 to 4 carbon atoms, and benzyl, wherein the phenyl moiety of the benzyl group is optionally substituted at any one position with chloride, bromide, iodide, cyano, or an alkyl group of 1 to 4 carbon atoms; compounds comprising the structural formula

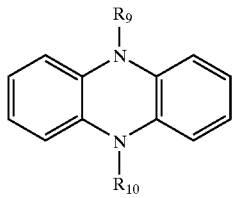

wherein $R_9$ is the same as or different from $R_{10}$ and both $R_9$ and $R_{10}$ are selected from alkyl of 1 to 10 carbon atoms, phenyl optionally substituted at any one position with chloride, bromide, iodide, cyano, or alkyl of 1 to 4 carbon atoms, or benzyl, optionally substituted at any one position of the phenyl group of the benzyl group with chloride, bromide, iodide, cyano, or alkyl of 1 to 4 carbon atoms; compounds comprising the structural formula

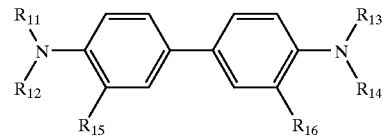

wherein $R_{11}$, $R_{12}$, $R_{13}$ and $R_{14}$ are the same or different and are each selected from alkyl of 1 to 10 carbon atoms or phenyl; and $R_{15}$ and $R_{16}$ are the same or different and are each selected from hydrogen or alkyl of 1 to 10 carbon atoms, provided that both $R_{15}$ and $R_{16}$ are hydrogen or both are alkyl, and if $R_{15}$ and $R_{16}$ are both hydrogen, not more than one of $R_{11}$ and $R_{12}$ is hydrogen and not more than one of $R_{13}$ and $R_{14}$ is hydrogen; compounds comprising the structural formula

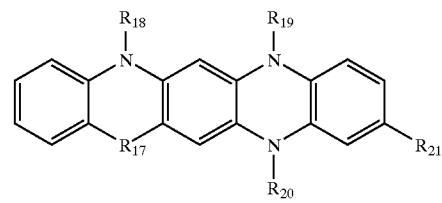

wherein $R_{17}$ is oxygen or sulfur, $R_{21}$ is hydrogen or dialkylamino, wherein the alkyl groups are the same or different and are each selected from alkyl of 1 to 6 carbon atoms, and $R_{18}$, $R_{19}$ and $R_{20}$ are the same or different and are each selected from hydrogen, alkyl of 1 to 6 carbon atoms, phenyl, optionally substituted at any one position with an alkyl group of 1 to 6 carbon atoms, and benzyl, optionally substituted at any one position of the phenyl group of the benzyl group with an alkyl group of 1 to 6 carbon atoms; compounds comprising the structural formula

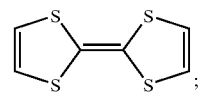

compounds comprising the structural formula

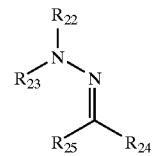

wherein $R_{22}$, $R_{23}$, $R_{24}$ and $R_{25}$ are individually selected from a group consisting of hydrogen, alkyl containing 5 to 20 carbon atoms, alkenyl containing 2 to 20 carbon atoms, alkynyl containing 2 to 20 carbon atoms, and aryl containing 5 to 20 carbon atoms which are unsubstituted or optionally substituted with one or more ester, ether, aryl, amine, thioester, alkyl, alkoxy, alkene, alkyne, cyano, fluoride, chloride, bromide, iodide, organometallocene functional groups, or combinations thereof; hydrazone compounds selected from the group consisting of acetone 2,2-dimethylhydrazone, 2-pentanone 2-ethyl- 2methylhydrazone, 2-ethylbutanal 1-ethyl-1-propylhydrazone, 2-ethyl-2-nonanone 2-hexyl-2-propylhydrazone, (E)-3-nonen-2-one 2butyl-2-propylhydrazone, 2-hexanone 2-[(E)-2-butenyl]-2-[(Z)-2-butenyl]-hydrazone, 4-pentyn-2-one 2,2-dipropylhydrazone, 1-penten-3-one 3,3-dimethylhydrazone, 2-hexanone 2,2-diphenylhydrazone, 3-heptanone 3-methyl-3-phenylhydrazone, 1-ethoxy-2-butanone 2-methyl-2-phenylhydrazone, 1-phenylacetone 2-(3-methoxyphenyl)-2-phenylhydrazone, 2-phenacetaldehyde 1-methyl-1-phenylhydrazone, methyl 3-[(Z)-2-methyl-2-phenylhydrazone]-butanethioate, 1-(3-chlorophenyl)-3-methoxy-1-propanone 1-methyl-1-(3-methylphenyl)hydrazone, ferrocenephenylketone 2-[(E)-2-butenyl]-2-[(Z)-2-butenyl]hydrazone, bis(cyclopentadienyl)cobaltmethylketone 2,2-diphenylhydrazone, bis(cyclopentadienyl)dimethylzirconiummethylketone 2,2-diphenyihydrazone, 1-phenyl-1-ethanone 1,1-di(2-methoxyethyl)hydrazone, 1-[3-(dimethylamino)phenyl]-1-ethanone 1,1-diethylhydrazone, 2-[(Z)-2,2-diethylhydrazono]propyl cyanide, 2-[(E)-2-ethyl-2-phenylhydrazono]-3-methoxypropyl cyanide, (Z)-1-chloro-1-penten-3-one 3-methyl-3-phenylhydrazone, 2-propynal 1-[4-(dimethylamino)phenyl]-1-methylhydrazone, ferrocenemethylketone-N,N-diphenylketone, 4-diethylaminobenzaldehyde-N,N-diphenylhydrazone, 4-diphenylaminobenzaldehyde-N,N-diphenylhydrazone, 9-ethylcarbazole-3-aldehyde-N,N-diphenylhydrazone, 9-ethylcarbazole-3-aldehyde-N-methyl-N-phenylhydrazone, and benzophenone-N,N-diphenylhydrazone.

11. The device of claim 1, further comprising at least one UV stabilizer.

12. The device of claim 11, wherein said UV stabilizer is selected from the group consisting of benzophenones, benzotriazoles, salicylates, nickel organics, monobenzoates, oxalanilides, carbon black, hindered amines, and zinc oxide.

13. The device of claim 1, further comprising at least one stiffening agent.

14. The device of claim 13, wherein said stiffening agent comprises at least one organic polymer.

15. The device of claim 14, wherein said stiffening agent comprises at least one organic polymer selected from the group consisting polyacrylonitrile, polyvinlidene fluoride, hexafluoropropylene, polyvinyl alcohol, polyvinylacetate, polymethylmethacrylate, and copolymers thereof.

16. The device of claim 1, wherein said molten salt solution further comprises from about 0.5% to about 30% of at least one soluble, aprotic organic cosolvent having a boiling point greater than 150° C.

17. The device of claim 16, wherein said cosolvent is selected from the group consisting of propylene carbonate, N-methyl pyrrolidinone, perfluorodecalin, and perfluorodecane.

18. The device of claim 1, wherein said device comprises indium tin oxide electrodes or doped indium tin oxide electrodes.

19. The device of claim 1, further comprising at least one thixotropic agent.

* * * * *